United States Patent [19]

Singiser et al.

[11] 4,076,804

[45] Feb. 28, 1978

[54] ERYTHROMYCIN THERAPY

[75] Inventors: Robert E. Singiser, Gurnee; Alexander Hing Chinn Chun, Waukegan; Shashi Pal Mehta, Libertyville, all of Ill.

[73] Assignee: Abbott Laboratories, North Chicago, Ill.

[21] Appl. No.: 749,637

[22] Filed: Dec. 13, 1976

Related U.S. Application Data

[63] Continuation-in-part of Ser. No. 597,057, Jul. 18, 1975, abandoned.

[51] Int. Cl.$^2$ .............................................. A61K 31/71
[52] U.S. Cl. ..................................................... 424/181
[58] Field of Search .......................................... 424/181

[56] References Cited

U.S. PATENT DOCUMENTS

| 3,865,935 | 2/1975 | Amann | 424/181 |
| 3,878,192 | 4/1975 | Blasina et al. | 424/181 |

Primary Examiner—Sam Rosen
Attorney, Agent, or Firm—Paul D. Burgauer; Robert L. Niblack

[57] ABSTRACT

This invention is directed to the method of combatting erythromycin sensitive bacteria in warm-blooded animals without restricting their food intake.

4 Claims, No Drawings

ERYTHROMYCIN THERAPY

BACKGROUND OF THE INVENTION

This application is a continuation-in-part of our previously filed application, Ser. No. 597,057, filed on July 18, 1975, now abandoned.

DETAILED DESCRIPTION OF THE INVENTION

For many years now, infections of warm-blooded animals have been successfully combatted with antibiotic therapy. One of the antibiotics used with a great deal of success is erythromycin which, unfortunately, cannot be administered orally as a free base without going through precautionary steps to avoid the extremely bitter taste thereof. One of the methods used to combat this taste problem is to deliver erythromycin in the form of a salt or an ester when it is intended to be used orally.

One of the most widely used derivatives of erythromycin for this purpose is the erythromycin ethyl succinate (hereinafter simply referred to as EES). The great success achieved with this ester is based on the fact that it produces a bacteriocidally effective blood level, when orally administered in relatively low quantities. However, this blood level can only b reached with the minimal dose if said EES is administered to an animal that has not taken any food for at least two hours prior to the administration of the EES.

It is therefore the primary object of this invention to provide a therapeutic process for combatting erythromycin sensitive bacteria in warm-blooded animals which are under no dietary restriction; it is a particular object of this invention to combat bacterial infections in warm-blooded animals which are non-fasting.

These and other objects are accomplished by administering to an animal in non-fasting condition and for the purpose of combatting a bacterial infection sensitive to erythromycin, a pharmaceutical compound of EES in granulated form, said granules comprising per 100 parts of EES between 3 and 100 parts of a pharmaceutically acceptable gum and between 20 and 4000 parts of a physiologically acceptble sugar.

For the purpose of this invention, the term "nonfasting" is intended to mean that the subject involved has consumed beverage or food within two hours prior to the administration of EES. The above reference to "sugar" includes such commonly used carbohydrates such as sucrose, fructose, glucose, mannitol, lactose, dextrose or mixtures thereof. In a preferred embodiment, the sugar is used in a powdered form which, for the purpose of this description, is meant to include substantially no particles >150 microns in diameter. The term "gum" is intended to include any of the numerous polysaccharides of plant origin which are gelatinous when moist but harden upon drying, or salts of complex organic acids. They are represented by the refined or purified materials commonly used in the art of granulating, such as guar, tragacanth, acacia, sodium carboxymethyl-cellulose, ethylcellulose, methylcellulose, colloidal magnesium-aluminumsilicate and the like.

The composition used in the process of the present invention can easily be produced on a commercial scale in the following manner: EES powdered sugar and gum are mixed in the desired ratio which may, as desired, include other additives, such as citric acid, sodium citrate, flavoring agents, coloring agents, etc. This mixture is then granulated by the addition of water according to known procedures and subsequently it is passed through a screen to eliminate large agglomerates. The granules are then spread for drying in routine fashion and they are subsequently mixed with additional flavoring agents, coloring agents, lubricants and the like, particularly if these granules are intended to be processed into chewable tablets. However, the just described granules are primarily intended for use as such; they can be reconstituted with water at the time of dispensing or placed in suspension at the time of manufacture. They form a stable suspension in water, and a suspenion of this nature is particularly suitable for administration to small animals including infants or those patients or animals that do not like to or are unable to swallow entire tablets. However, tablets made from granules share the advantage of the reconstituted aqueous suspension of EES made from the granules: they will produce bacteriocidal blood levels in non-fasting animals similar to the erythromycin blood levels obtained in fasting animals upon administration of the same dosage but without the addition of the gum.

In order to illustrate the effectiveness of the present method, reference is made to the following examples, which however, are not intended to limit this invention in any respect.

EXAMPLE 1

The following ingredients were thoroughly blended: 235 parts of EES, 25 parts of sodium carboxymethylcellulose, 300 parts of powdered mannitol, 100 parts of sodium citrate, and a mixture of 10 parts of flavor and coloring agents. This mass is ground and blended in the usual fashion, massed with water and dried in an oven in the usual fashion. 4The granules obtained in this fashion are then ground again, thoroughly mixed with 10 parts of magnesium stearate and compressed into tablets in the usual fashion, producing tablets (Tablet A) containing 200 milligram equivalence of erythromycin activity.

An identical tablet as shown above is made by the above procedure except that it contains no sodium carboxymethylcellulose, using instead 21 parts of a weak amino exchange resin which is added to the granules subsequent to granulation together with 35 parts (instead of 10 parts) of magnesium stearate (Tablet B).

EXAMPLE 2

Serum levels obtained with the above formulations A and B were studied on 24 subjects per formulation in a multiple dose fasting cross-over study using 2 of the above tablets per dose every 6 hours for 10 doses. The serum levels were determined at certain intervals after the first, 9th and 10th administration of the drug. Also determined were individual peak levels (PL) and the area-under-curve values (AUC) for 6-hour periods starting at the time of administering the first, ninth and tenth dose. The results are shown in table I. In all instances, the values given below are average values obtained from all subjects.

TABLE I

| Time    | Tablet A |        | Tablet B |        |
|---------|----------|--------|----------|--------|
| 0       | <0.015   | µg/ml  | <0.015   | µg/ml  |
| ½ hr    | 1.129    | "      | 0.790    | "      |
| 1 hr    | 1.228    | "      | 0.844    | "      |
| 1.5 hrs | 0.822    | "      | 0.681    | "      |
| 2 hrs   | 0.639    | "      | 0.532    | "      |
| 3 hrs   | 0.451    | "      | 0.355    | "      |
| 4.5 hrs | 0.285    | "      | 0.200    | "      |
| 6 hrs   | 0.158    | "      | 0.108    | "      |

TABLE I-continued

| Time | Tablet A | | Tablet B | |
|---|---|---|---|---|
| 48 hrs | 0.279 | " | 0.232 | " |
| 48.5 hrs | 1.411 | " | 1.315 | " |
| 49 hrs | 1.766 | " | 1.462 | " |
| 49.5 hrs | 1.467 | " | 1.180 | " |
| 50 hrs | 1.212 | " | 0.942 | " |
| 51 hrs | 0.935 | " | 0.752 | " |
| 52.5 hrs | 0.574 | " | 0.476 | " |
| 54 hrs | 0.381 | " | 0.319 | " |
| 54.5 hrs | 1.633 | " | 1.447 | " |
| 55 hrs | 1.850 | " | 1.463 | " |
| 55.5 hrs | 1.511 | " | 1.228 | " |
| 56 hrs | 1.215 | " | 0.921 | " |
| 57 hrs | 0.902 | " | 0.665 | " |
| 58.5 hrs | 0.545 | " | 0.460 | " |
| 60 hrs | 0.389 | " | 0.308 | " |
| 1 PL 0-6 hrs | 1.402 | " | 0.915 | " |
| 1 PL 48-54 hrs | 1.900 | " | 1.579 | " |
| 1 PL 54-60 hrs | 1.981 | " | 1.585 | " |
| AUC 0-6 hrs | 3.18 | $\mu g \times hr/ml$ | 2.39 | $\mu g \times hr/ml$ |
| AUC 48-54 hrs | 5.62 | $\mu g \times hr/ml$ | 4.64 | $\mu g \times hr/ml$ |
| AUC 54-60 hrs | 5.74 | $\mu g \times hr/ml$ | 4.59 | $\mu g \times hr/ml$ |

It is quite apparent from the above figures that the tablet made according to the present invention (Tablet A) shows significantly improved levels at all times and in all intervals and other aspects measured. However, in all instances, the adult human subjects were under fasted conditions, i.e. they only took in food two hours after each drum administration or 4 hours prior to the next scheduled drug intake.

EXAMPLE 3

The following ingredients are blended to homogeniety: 130 parts of EES, part of a mixture of 13.5 of sodium carboxymethylcellulose and 4.4 parts of Veegum F (colloidal magnesiumaluminum silicate, marketed by R. T. Vanderbilt Company, 230 Park Ave., New York, N. Y.) 795 parts of powdered sucrose, 53 parts of sodium citrate and 0.1 part of citric acid. The mixture is massed with water containing the remaining portion of the above mixture of sodium carboxymethylcellulose, Veegum, as well as the desired coloring agent. This mass is dried, ground and blended with the desired flavoring agents (color and flavor agents together make up 4 parts). These granules are then suspended in water to make up a suspension containing 400 mg erythromycin activity per 10 ml of water. This suspension is referred to below as composition C.

In identical manner as shown above, 130 parts of EES, 813 parts of powdered sucrose, 53 parts of sodium citrate, 0.1 part of citric acid, and a total of 40parts of flavor and color are processed into granules containing no gum. A suspension similar to the above is made from these granules also containing 400 mg of erythromycin activity per 10 ml. but without gum. This composition is referred to below as composition D.

EXAMPLE 4

Sixteen healthy adult male and female subjects between the ages of 23 and 46 and weighing between 118 and 207 lbs. were randomly assigned to 2 groups of medication in a complete crossover design study. The individual single dose administration of drug compositions were made 1 week apart, each individual being tested on both preparations.

The subjects were fasted for a minimum of 12 hours prior to the feeding of a standard breakfast. A half hour after starting breakfast, a 400 mg dose (erythromycin equivalence) was administered orally as a suspension corresponding to those described as compositions C and D of Example 3. Formulation C was reconstituted with water (to 400 mg per 10 ml drug activity) on the afternoon prior to the study and stored under refrigeration. Formulation D was reconstituted with water at breakfast time. Formulations C and D were ingested by each subject with 4 ounces of water and water was used to rinse the remaining drug particles from the container. Blood samples were taken immediately before dosing and at various times thereafter. The serum samples were assayed under blinded conditions; the assay results are shown in Table II:

TABLE II

| Time | Composition C | Composition D |
|---|---|---|
| 0.5 hrs. | 0.761 µg/ml | 0.339 µg/ml |
| 1 hrs. | 0.725 " | 0.314 " |
| 1.5 hrs. | 0.568 " | 0.269 " |
| 3 hrs. | 0.290 " | 0.188 " |
| 4.5 hrs. | 0.130 " | 0.089 " |
| 6 hrs. | 0.064 " | 0.042 " |
| Peak level | 0.469 " | 0.339 " |
| AUC 0 to 6 hrs. | 1.99 µg × hr/ml | 1.05 µg × hr/ml |

All the above values represent the average of all subjects testing the same composition. As can be seen, the composition containing the gum (Composition C) is far superior to composition D at any time during the assay period and consequently produces a much larger area-under-curve value than the other compositions containing no gum or being diluted.

EXAMPLE 5

In a further test with formulation A of Example 1, the tablet is ingested after chewing by the volunteer subjects. From analyzing the blood samples at intervals as in Example 2, it is seen that essentially the same results are obtained as shown for Tablet A in Table I.

EXAMPLE 6

In a further test, the granules used for making the formulations identified as Composition C and D in Example 4, administered without reconstituting them into a suspension show to give substantially the same results as shown in Table II. However, upon diluting the granules of Composition C to a concentration of 400 mg erythromycin activity per 120 ml one day prior to the test, the area-under-curve for the first 6 hrs. averaged 1.36 µg × hr/ml and the individual peak levels averaged 0.571 µg/ml.

The granules of Example 1 (Tablet A) used for tablet manufacture and the liquid Composition (C) of Example 3 may be made in the same manner as described except for replacing sodium carboxymethylcellulose or Veegum F, respectively with other gums. For instance, tablets made according to Example 1 (A) made with methylcellulose as the gum is particularly suitable as a chewable tablet. Composition C of Example 3 made with ethylcellulose, acacia or guar in place of Veegum give the same blood level as those described.

As seen above, the inclusion of gum into an EES suspension increases the obtainable blood serum level of erythromycin activity considerably in fasting as well as in non-fasting subjects. The inclusion of the gum appears to be one of protection of the EES against the strong acidity in the stomach, because when the suspension of Composition C, for instance, is diluted just prior to administration in a relatively large volume of water, the obtainable blood level is much inferior than that shown above, suggesting that the aqueous dilution reduces the protective mechanism of the gum, making the acid-labile drug susceptible to degradation by gastric secretions.

The granules shown above can be made in deviation from the above examples and can be suspended in a variety of media, but care must be taken that the suspension is neither too dilute nor that the ratio between gum and EES deviates from the above identified range. The granules can be compressed into tablets as shown above, or they can be reconstituted into a suspension as shown; the tablets so obtained are chewable and are particularly well suited for pediatric and geriatric patients who, of course, are also the prime subjects to receive suspensions such as those obtained by reconstituting the granules in water.

For best results in combatting infections caused by bacteria susceptible to erythromycin, treatment consists in administering to normal-weight adult patients the equivalent of 400 mg erythromycin activity per dose, preferably 4 times per day. In children, a correspondingly reduced dose is indicated, although, due to the very low toxicity of EES, overdosing is of no particular consequence in this instance. It is particularly with children that the composition used in the present treatment is of great significance, since infants or small children generally are difficult to handleunder "fasting" conditions. With the new therapeutic procedure, no restrictions are required on food intake, and contrary to any of the existing erythromycin preparations, commonly prescribed, no need for fasting for any given length of time prior to dosing is necessary.

The above reference to the preferred embodiment with sugar particles being of a diameter < 150 microns, is primarily for the purpose of elegance of the ultimate dosage form. If this dosage is a colored tablet, granules made from mixtures containing larger sugar particles than 150 microns in diameter have a speckeld appearance to the naked eye and therefore are unsightly. When tablets are made from granules, which contain substantially no particles of a diameter > 150 microns, a smooth color appearance will result which appears to completely penetrate the tablet and to cover the surface of the tablet in a continuous fashion. Whether the granules are used for chewable tablets or a liquid dosage form, granules made from sugar particles of < 150 microns produce a much more palatable mouthfeel, substantially completely devoid of the grittiness feel observed with larger particles, whether the composition is colored or not.

While it is possible to make tablets or liquid dosage forms with the current granules using non-powdered sugar, neither dosage form would be acceptable to the pharmaceutical dispensary and objectionable from an esthetic point of view and for reasons of mouth-feel.

We claim:

1. The process of combatting an erythromycin sensitive infection in a warm-blooded animal in non-fasting condition, comprising, administering to said animal a pharmaceutical preparation of erythromycin ethylsuccinate in granulated form, said granules comprising per 100 parts of erythromycin ethylsuccinate between 3 and 100 parts of a pharmaceutically acceptable gum and between 20 and 4000 parts of a physiologically acceptable sugar.

2. The process of claim 1 wherein said granules are administered in the form of a suspension.

3. The process of claim 1 wherein said granules are administered in the form of a chewable tablet.

4. A chewable tablet consisting essentially of granules, consisting essentially of 100 parts by weight of erythromycin ethylsuccinate, 3-100 parts by weight of a pharmaceutically acceptable gum and 20-4000 parts by weight of a physiologically acceptable sugar, said sugar being used in powderd form containing essentially no particles with a diameter > 150 microns.

* * * * *